United States Patent
Bjorn et al.

(10) Patent No.: US 7,001,986 B2
(45) Date of Patent: Feb. 21, 2006

(54) FLUORESCENT PROTEINS

(75) Inventors: Sara Petersen Bjorn, Lyngby (DK);
Len Pagliaro, Copenhagen K (DK);
Ole Thastrup, Birkerod (DK)

(73) Assignee: Bioimage A/S, Søborg (DK)

( * ) Notice: Subject to any disclaimer, the term of this patent is extended or adjusted under 35 U.S.C. 154(b) by 460 days.

(21) Appl. No.: 09/887,784

(22) Filed: Jun. 19, 2001

(65) Prior Publication Data

US 2002/0177189 A1   Nov. 28, 2002

Related U.S. Application Data

(60) Provisional application No. 60/212,681, filed on Jun. 20, 2000, provisional application No. 60/290,170, filed on May 10, 2001.

(30) Foreign Application Priority Data

Jun. 19, 2000  (DK)  ................ 2000 00953
May 10, 2001  (DK)  ................ 2001 00739

(51) Int. Cl.
*C07K 1/00*   (2006.01)
(52) U.S. Cl. .................... 530/350; 530/300; 435/69.1; 435/7.1; 435/320.1; 435/252; 514/2; 514/12; 536/23.1
(58) Field of Classification Search ........... 530/350, 530/300; 435/7.1, 252.33, 252.3, 325, 410, 435/69.1, 320.1, 252; 514/2, 12; 536/23.1
See application file for complete search history.

(56) References Cited

U.S. PATENT DOCUMENTS 6,124,128 A * 9/2000 Tsien et al. ............ 435/252.33
6,172,188 B1  1/2001 Thastrup et al. ............ 530/350

FOREIGN PATENT DOCUMENTS

WO   WO 97/11094   *  3/1997

OTHER PUBLICATIONS

Roger Helm et al., Proc. Natl. Acad. Sci. USA, vol. 9, pp. 12501-12504, Dec. 1994.
Torsten Ehrig et al., FEBS Letters, 367 (1995) pp. 163-166.
Katjusa Brejc et al., Proc. Natl. Acad. Sci. USA, vol. 94, pp. 2306-2311, Mar. 1997.
Te-Tuan Yang et al., Nucleic Acids Research, 1996, vol. 24, No. 22, pp. 4592-4593.

* cited by examiner

*Primary Examiner*—Robert A. Wax
*Assistant Examiner*—Hope Robinson
(74) *Attorney, Agent, or Firm*—Birch, Stewart, Kolasch & Birch, LLP

(57)   ABSTRACT

A GFP with an F64L mutation and an E222G mutation is provided. This GFP has a bigger Stokes shift compared to other GFPs making it very suitable for high throughput screening due to a better resolution. This GFP also has an excitation maximum between the yellow GFP and the cyan GFP allowing for cleaner band separation when used together with those GFPs.

13 Claims, 8 Drawing Sheets

Panel A

Panel B

Panel C

Panel D

SEQUENCE LISTING

```
<160> NUMBER OF SEQ ID NOS: 24

<210> SEQ ID NO 1
<211> LENGTH: 720
<212> TYPE: DNA
<213> ORGANISM: Aequoria Victoria
<220> FEATURE:
<221> NAME/KEY: CDS
<222> LOCATION: (1)...(717)

<400> SEQUENCE: 1 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
                20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
            35                  40                  45 tgc acc acc ggc aag ctg ccc gtg ccc tgg ccc aca cta gtg acc acc     192
Cys Thr Thr Gly Lys Leu Pro Val Pro Trp Pro Thr Leu Val Thr Thr
        50                  55                  60 ctg tct tac ggc gtg cag tgc ttc agc cgc tac ccc gac cac atg aag     240
Leu Ser Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
```

```
                130                 135                 140
aac tac aac agc cac aac gtc tat atc atg gcc gac aag cag aag aac    480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc    528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc    576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg    624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc    672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag        717
Val Thr Ala Ala Gly Ile Thr Leu Gly Met Asp Glu Leu Tyr Lys
225                 230                 235 taa                                                                 720

<210> SEQ ID NO 2
<211> LENGTH: 239
<212> TYPE: PRT
<213> ORGANISM: Aequoria Victoria

<400> SEQUENCE: 2

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
```

```
                    225                 230                 235

<210> SEQ ID NO 3
<211> LENGTH: 720
<212> TYPE: DNA
<213> ORGANISM: Aequoria Victoria
<220> FEATURE:
<221> NAME/KEY: CDS
<222> LOCATION: (1)...(717)

<400> SEQUENCE: 3 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
             20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc aca cta gtg acc acc     192
Cys Thr Thr Gly Lys Leu Pro Val Pro Trp Pro Thr Leu Val Thr Thr
     50                  55                  60 ctg tct tac ggc gtg cag tgc ttc agc cgc tac ccc gac cac atg aag     240
Leu Ser Tyr Gly Val Gln Cys Phe Ser Arg Tyr Pro Asp His Met Lys
 65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg     624
Pro Val Leu Leu Pro Asp Asn His Tyr Leu Ser Thr Gln Ser Ala Leu
        195                 200                 205 agc aaa gac ccc aac gag aag cgc gat cac atg gtc ctc cta ggg ttc     672
Ser Lys Asp Pro Asn Glu Lys Arg Asp His Met Val Leu Leu Gly Phe
    210                 215                 220 gtg acc gcc gcc ggg atc act ctc ggc atg gac gag ctg tac aag         717
Val Thr Ala Ala Gly Ile Thr Leu Gly Met Asp Glu Leu Tyr Lys
225                 230                 235 taa                                                                 720

<210> SEQ ID NO 4
<211> LENGTH: 239
<212> TYPE: PRT
```

<213> ORGANISM: Aequoria Victoria

<400> SEQUENCE: 4

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Gly Phe
210                 215                 220

Val Thr Ala Ala Gly Ile Thr Leu Gly Met Asp Glu Leu Tyr Lys
225                 230                 235
```

<210> SEQ ID NO 5
<211> LENGTH: 717
<212> TYPE: DNA
<213> ORGANISM: Aequoria Victoria
<220> FEATURE:
<221> NAME/KEY: CDS
<222> LOCATION: (1)...(714)

<400> SEQUENCE: 5

```
atg agt aaa gga gaa gaa ctt ttc act gga gtt gtc cca att ctt gtt      48
Met Ser Lys Gly Glu Glu Leu Phe Thr Gly Val Val Pro Ile Leu Val
1               5                   10                  15 gaa tta gat ggc gat gtt aat ggg caa aaa ttc tct gtt agt gga gag      96
Glu Leu Asp Gly Asp Val Asn Gly Gln Lys Phe Ser Val Ser Gly Glu
            20                  25                  30 ggt gaa ggt gat gca aca tac gga aaa ctt acc ctt aaa ttt att tgc     144
Gly Glu Gly Asp Ala Thr Tyr Gly Lys Leu Thr Leu Lys Phe Ile Cys
        35                  40                  45 act act ggg aag cta cct gtt cca tgg cca acg ctt gtc act act ctc     192
Thr Thr Gly Lys Leu Pro Val Pro Trp Pro Thr Leu Val Thr Thr Leu
    50                  55                  60 tct tat ggt gtt caa tgc ttt tct aga tac cca gat cat atg aaa cag     240
Ser Tyr Gly Val Gln Cys Phe Ser Arg Tyr Pro Asp His Met Lys Gln
65                  70                  75                  80
```

```
cat gac ttt ttc aag agt gcc atg ccc gaa ggt tat gta cag gaa aga       288
His Asp Phe Phe Lys Ser Ala Met Pro Glu Gly Tyr Val Gln Glu Arg
                85                  90                  95 act ata ttt tac aaa gat gac ggg aac tac aag aca cgt gct gaa gtc       336
Thr Ile Phe Tyr Lys Asp Asp Gly Asn Tyr Lys Thr Arg Ala Glu Val
            100                 105                 110 aag ttt gaa ggt gat acc ctt gtt aat aga atc gag tta aaa ggt att       384
Lys Phe Glu Gly Asp Thr Leu Val Asn Arg Ile Glu Leu Lys Gly Ile
        115                 120                 125 gat ttt aaa gaa gat gga aac att ctt gga cac aaa atg gaa tac aat       432
Asp Phe Lys Glu Asp Gly Asn Ile Leu Gly His Lys Met Glu Tyr Asn
    130                 135                 140 tat aac tca cat aat gta tac atc atg gca gac aaa cca aag aat ggc       480
Tyr Asn Ser His Asn Val Tyr Ile Met Ala Asp Lys Pro Lys Asn Gly
145                 150                 155                 160 atc aaa gtt aac ttc aaa att aga cac aac att aaa gat gga agc gtt       528
Ile Lys Val Asn Phe Lys Ile Arg His Asn Ile Lys Asp Gly Ser Val
                165                 170                 175 caa tta gca gac cat tat caa caa aat act cca att ggc gat ggc cct       576
Gln Leu Ala Asp His Tyr Gln Gln Asn Thr Pro Ile Gly Asp Gly Pro
            180                 185                 190 gtc ctt tta cca gac aac cat tac ctg tcc acg caa tct gcc ctt tcc       624
Val Leu Leu Pro Asp Asn His Tyr Leu Ser Thr Gln Ser Ala Leu Ser
        195                 200                 205 aaa gat ccc aac gaa aag aga gat cac atg atc ctt ctt gag ttt gta       672
Lys Asp Pro Asn Glu Lys Arg Asp His Met Ile Leu Leu Glu Phe Val
    210                 215                 220 aca gct gct ggg att aca cat ggc atg gat gaa ggg tac aag              714
Thr Ala Ala Gly Ile Thr His Gly Met Asp Glu Gly Tyr Lys
225                 230                 235 taa                                                                    717

<210> SEQ ID NO 6
<211> LENGTH: 238
<212> TYPE: PRT
<213> ORGANISM: Aequoria Victoria

<400> SEQUENCE: 6

Met Ser Lys Gly Glu Glu Leu Phe Thr Gly Val Val Pro Ile Leu Val
 1               5                  10                  15

Glu Leu Asp Gly Asp Val Asn Gly Gln Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

Tyr Asn Ser His Asn Val Tyr Ile Met Ala Asp Lys Pro Lys Asn Gly
```

```
                145                 150                 155                 160
Ile Lys Val Asn Phe Lys Ile Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Leu Leu Glu Phe Val
    210                 215                 220

Thr Ala Gly Ile Thr His Gly Met Asp Glu Gly Tyr Lys
225                 230                 235

<210> SEQ ID NO 7
<211> LENGTH: 717
<212> TYPE: DNA
<213> ORGANISM: Aequovia Victoria
<220> FEATURE:
<221> NAME/KEY: CDS
<222> LOCATION: (1)...(717)

<400> SEQUENCE: 7 atg agt aaa gga gaa gaa ctt ttc act gga gtt gtc cca att ctt gtt      48
Met Ser Lys Gly Glu Glu Leu Phe Thr Gly Val Val Pro Ile Leu Val
 1               5                  10                  15 gaa tta gat ggc gat gtt aat ggg caa aaa ttc tct gtt agt gga gag      96
Glu Leu Asp Gly Asp Val Asn Gly Gln Lys Phe Ser Val Ser Gly Glu
            20                  25                  30 ggt gaa ggt gat gca aca tac gga aaa ctt acc ctt aaa ttt att tgc     144
Gly Glu Gly Asp Ala Thr Tyr Gly Lys Leu Thr Leu Lys Phe Ile Cys
        35                  40                  45 act act ggg aag cta cct gtt cca tgg cca acg ctt gtc act act ctc     192
Thr Thr Gly Lys Leu Pro Val Pro Trp Pro Thr Leu Val Thr Thr Leu
    50                  55                  60 tct tat ggt gtt caa tgc ttt tct aga tac cca gat cat atg aaa cag     240
Ser Tyr Gly Val Gln Cys Phe Ser Arg Tyr Pro Asp His Met Lys Gln
 65                  70                  75                  80 cat gac ttt ttc aag agt gcc atg ccc gaa ggt tat gta cag gaa aga     288
His Asp Phe Phe Lys Ser Ala Met Pro Glu Gly Tyr Val Gln Glu Arg
                 85                  90                  95 act ata ttt tac aaa gat gac ggg aac tac aag aca cgt gct gaa gtc     336
Thr Ile Phe Tyr Lys Asp Asp Gly Asn Tyr Lys Thr Arg Ala Glu Val
            100                 105                 110 aag ttt gaa ggt gat acc ctt gtt aat aga atc gag tta aaa ggt att     384
Lys Phe Glu Gly Asp Thr Leu Val Asn Arg Ile Glu Leu Lys Gly Ile
        115                 120                 125 gat ttt aaa gaa gat gga aac att ctt gga cac aaa atg gaa tac aat     432
Asp Phe Lys Glu Asp Gly Asn Ile Leu Gly His Lys Met Glu Tyr Asn
    130                 135                 140 tat aac tca cat aat gta tac atc atg gca gac aaa cca aag aat ggc     480
Tyr Asn Ser His Asn Val Tyr Ile Met Ala Asp Lys Pro Lys Asn Gly
145                 150                 155                 160 atc aaa gtt aac ttc aaa att aga cac aac att aaa gat gga agc gtt     528
Ile Lys Val Asn Phe Lys Ile Arg His Asn Ile Lys Asp Gly Ser Val
                165                 170                 175 caa tta gca gac cat tat caa caa aat act cca att ggc gat ggc cct     576
Gln Leu Ala Asp His Tyr Gln Gln Asn Thr Pro Ile Gly Asp Gly Pro
            180                 185                 190 gtc ctt tta cca gac aac cat tac ctg tcc acg caa tct gcc ctt tcc     624
Val Leu Leu Pro Asp Asn His Tyr Leu Ser Thr Gln Ser Ala Leu Ser
        195                 200                 205
```

```
aaa gat ccc aac gaa aag aga gat cac atg atc ctc cta ggg ttt gta        672
Lys Asp Pro Asn Glu Lys Arg Asp His Met Ile Leu Leu Gly Phe Val
210                 215                 220 aca gct gct ggg att aca cat ggc atg gat gaa cta tac aaa taa            717
Thr Ala Ala Gly Ile Thr His Gly Met Asp Glu Leu Tyr Lys *
225                 230                 235
```

<210> SEQ ID NO 8
<211> LENGTH: 238
<212> TYPE: PRT
<213> ORGANISM: Aequovia Victoria

<400> SEQUENCE: 8

```
Met Ser Lys Gly Glu Glu Leu Phe Thr Gly Val Val Pro Ile Leu Val
1               5                   10                  15

Glu Leu Asp Gly Asp Val Asn Gly Gln Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

Tyr Asn Ser His Asn Val Tyr Ile Met Ala Asp Lys Pro Lys Asn Gly
145                 150                 155                 160

Ile Lys Val Asn Phe Lys Ile Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Leu Leu Gly Phe Val
    210                 215                 220

Thr Ala Ala Gly Ile Thr His Gly Met Asp Glu Leu Tyr Lys
225                 230                 235
```

<210> SEQ ID NO 9
<211> LENGTH: 33
<212> TYPE: DNA
<213> ORGANISM: Artificial Sequence
<220> FEATURE:
<223> OTHER INFORMATION: PCR Primer

<400> SEQUENCE: 9
tgtactagtg accaccctgt cttacggcgt gca                                    33

<210> SEQ ID NO 10
<211> LENGTH: 30
<212> TYPE: DNA
<213> ORGANISM: Artificial Sequence

```
<220> FEATURE:
<223> OTHER INFORMATION: PCR Primer

<400> SEQUENCE: 10
ctgactagtg tgggccaggg cacgggcagc                                          30

<210> SEQ ID NO 11
<211> LENGTH: 42
<212> TYPE: DNA
<213> ORGANISM: Artificial Sequence
<220> FEATURE:
<223> OTHER INFORMATION: PCR Primer

<400> SEQUENCE: 11
cccggcggcg gtcacgaacc ctaggaggac catgtgatcg cg                            42

<210> SEQ ID NO 12
<211> LENGTH: 42
<212> TYPE: DNA
<213> ORGANISM: Artificial Sequence
<220> FEATURE:
<223> OTHER INFORMATION: PCR Primer

<400> SEQUENCE: 12
cgcgatcaca tggtcctcct agggttcgtg accgccgccg gg                            42

<210> SEQ ID NO 13
<211> LENGTH: 31
<212> TYPE: DNA
<213> ORGANISM: Artificial Sequence
<220> FEATURE:
<223> OTHER INFORMATION: PCR Primer

<400> SEQUENCE: 13
gtaccggtca ccatgagtaa aggagaagaa c                                       31

<210> SEQ ID NO 14
<211> LENGTH: 29
<212> TYPE: DNA
<213> ORGANISM: Artificial Sequence
<220> FEATURE:
<223> OTHER INFORMATION: PCR Primer

<400> SEQUENCE: 14
ttattggtac ccttcatcca tgccatgtg                                          29

<210> SEQ ID NO 15
<211> LENGTH: 41
<212> TYPE: DNA
<213> ORGANISM: Artificial Sequence
<220> FEATURE:
<223> OTHER INFORMATION: PCR Primer

<400> SEQUENCE: 15
gagatcacat gatcctccta gggtttgtaa cagctgctgg g                            41

<210> SEQ ID NO 16
<211> LENGTH: 41
<212> TYPE: DNA
<213> ORGANISM: Artificial Sequence
<220> FEATURE:
<223> OTHER INFORMATION: PCR Primer

<400> SEQUENCE: 16
cccagcagct gttacaaacc ctaggaggat catgtgatct c                            41
```

-continued

<210> SEQ ID NO 17
<211> LENGTH: 34
<212> TYPE: DNA
<213> ORGANISM: Artificial Sequence
<220> FEATURE:
<223> OTHER INFORMATION: PCR Primer

<400> SEQUENCE: 17
ccaacgcttg tcacaacgtt ttcttatggt gttc                    34

<210> SEQ ID NO 18
<211> LENGTH: 34
<212> TYPE: DNA
<213> ORGANISM: Artificial Sequence
<220> FEATURE:
<223> OTHER INFORMATION: PCR Primer

<400> SEQUENCE: 18
gaacaccata agaaaacgtt gtgacaagcg ttgg                    34

<210> SEQ ID NO 19
<211> LENGTH: 34
<212> TYPE: DNA
<213> ORGANISM: Artificial Sequence
<220> FEATURE:
<223> OTHER INFORMATION: PCR Primer

<400> SEQUENCE: 19
cccacactag tgacaacgtt ttcttacggc gtgc                    34

<210> SEQ ID NO 20
<211> LENGTH: 34
<212> TYPE: DNA
<213> ORGANISM: Artificial Sequence
<220> FEATURE:
<223> OTHER INFORMATION: PCR Primer

<400> SEQUENCE: 20
gcacgccgta agaaaacgtt gtcactagtg tggg                    34

<210> SEQ ID NO 21
<211> LENGTH: 32
<212> TYPE: DNA
<213> ORGANISM: Artificial Sequence
<220> FEATURE:
<223> OTHER INFORMATION: PCR Primer

<400> SEQUENCE: 21
gttgtttcat gagtaaagga gaagaacttt tc                      32

<210> SEQ ID NO 22
<211> LENGTH: 31
<212> TYPE: DNA
<213> ORGANISM: Artificial Sequence
<220> FEATURE:
<223> OTHER INFORMATION: PCR Primer

<400> SEQUENCE: 22
gttggatcct tatttgtata gttcatccat g                       31

<210> SEQ ID NO 23
<211> LENGTH: 32
<212> TYPE: DNA
<213> ORGANISM: Artificial Sequence
<220> FEATURE:
<223> OTHER INFORMATION: PCR Primer

```
<400> SEQUENCE: 23
gttgttccat ggtgagcaag ggcgaggagc tg                                32

<210> SEQ ID NO 24
<211> LENGTH: 31
<212> TYPE: DNA
<213> ORGANISM: Artificial Sequence
<220> FEATURE:
<223> OTHER INFORMATION: PCR Primer

<400> SEQUENCE: 24
gttggatcct tacttgtaca gctcgtccat g                                 31
```

FLUORESCENT PROTEINS

Figure 1:
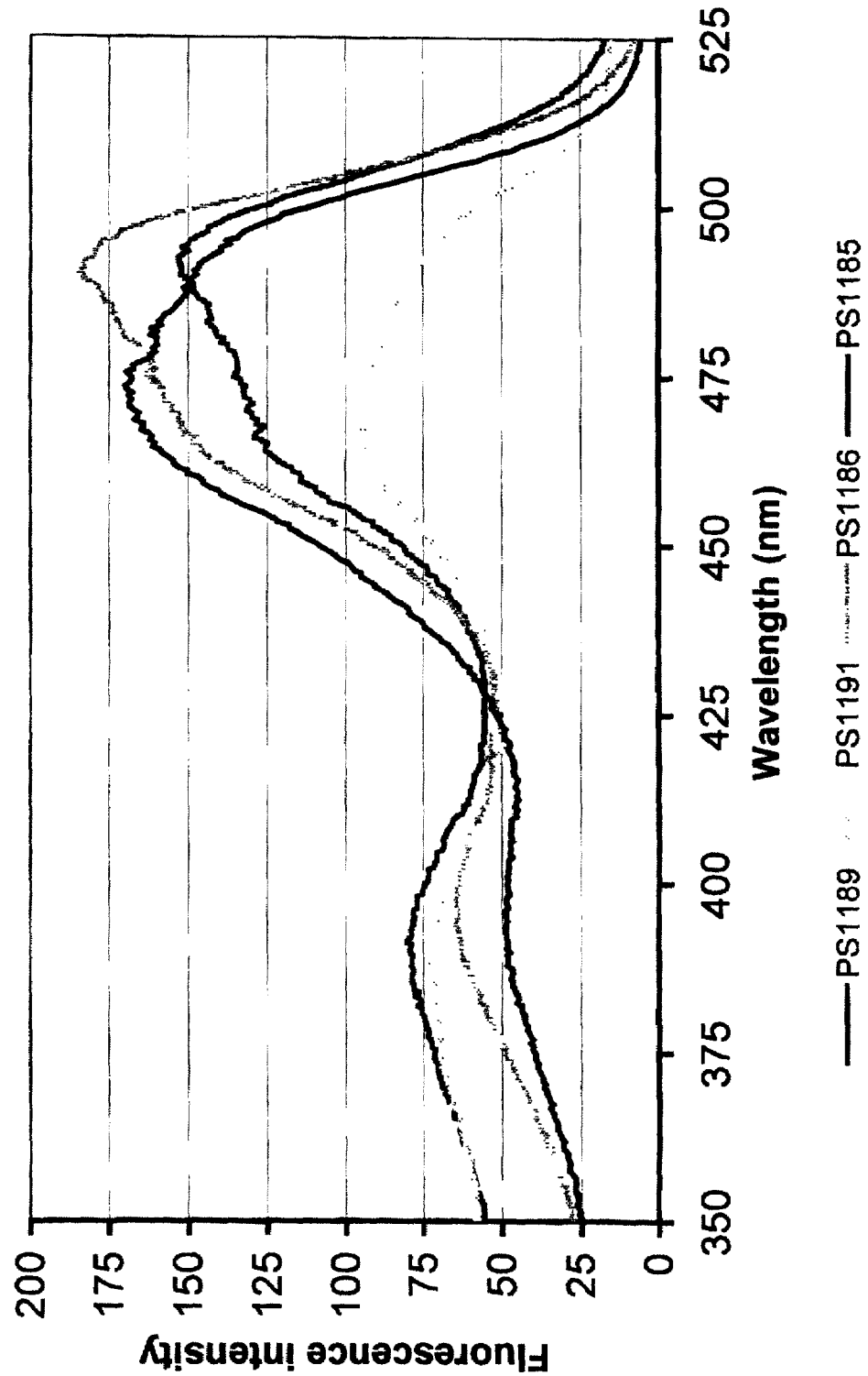

This non-provisional application incorporates by reference the subject matter of Application Nos. PA 2000 00953 and PA 2001 00739 filed in Denmark on Jun. 19, 2000 and May 10, 2001, respectively, on which a priority claim is based under 35 U.S.C. §119(a). This application also incorporates by reference the subject matter of co-pending U.S. Provisional Application Nos. 60/212,681 and 60/290,170 filed in the United States on Jun. 20, 2000 and May 10, 2001, respectively, on which a priority claim is based under 35 U.S.C. §119(e).

FIELD OF INVENTION

The present invention relates to novel variants of the fluorescent protein GFP having improved fluorescence properties.

BACKGROUND

The discovery that Green Fluorescent Protein (GFP) from the jellyfish *A. victoria* retains its fluorescent properties when expressed in heterologous cells has provided biological research with a new, unique and powerful tool (Chalfie et al (1994). Science 263:802; Prasher (1995) Trends in Genetics 11:320; WO 95/07463). A very important aspect of using recombinant, fluorescent proteins in studying cellular functions is the non-invasive nature of the assay. This allows detection of cellular events in intact, living cells.

The excitation spectrum of the green fluorescent protein from *Aequorea victoria* shows two peaks: A major peak at 396 nm, which is in the potentially cell damaging UV range, and a lesser peak at 475 nm, which is in an excitation range that is much less harmful to cells.

To improve the wild type GFP, a range of mutations have been described. Heim (GFP (Heim et al. (1994). Proc.Natl.Acad.Sci. 91:12501) described the discovery of a blue fluorescent variant which has greatly increased the potential applications of using fluorescent recombinant probes to monitor cellular events or functions, since the availability of probes having different excitation and emission spectra permits simultaneous monitoring of more than one process. However, the blue fluorescing variant described by Heim et al, Y66H-GFP, suffers from certain limitations: The blue fluorescence is weak (emission maximum at 448 nm), thus making detection difficult, and necessitating prolonged excitation of cells expressing Y66H-GFP. Moreover, the prolonged period of excitation is damaging to cells especially because the excitation wavelength is in the UV range, 360 nm–390 nm.

Heim et al.(1995), Nature, Vol. 373, p. 663–4, discloses a Ser65Thr mutation of GFP (S65T) having longer wavelengths of excitation and emission, 490 nm and 510 nm, respectively, than the wild-type GFP and wherein the fluorophore formation proceeded about fourfold more rapidly than in the wild-type GFP.

Ehrig et al. (1995) FEBS Letters 367, 163–166, discloses a E222G mutant of the *Aequorea* green fluorescent protein. This mutation has an excitation maximum of 481 nm and an emission maximum at 506 nm.

Expression of GFP or its fluorescent variants in living cells provides a valuable tool for studying cellular events and it is well known that many cells, including mammalian cells, are incubated at approximately 37° C. in order to secure optimal and/or physiologically relevant growth. Cell lines originating from different organisms or tissues may have different relevant temperatures ranging from about 35° C. for fibroblasts to about 38° C.–39° C. for mouse β-cells. Experience has shown, however, that the fluorescent signal from cells expressing GFP is weak or absent when said cells are incubated at temperatures above room temperature, cf. Webb, C. D. et al., Journal of Bacteriology, Oct. 1995, p. 5906–5911. Ogawa H. et al., Proc. Natl. Acad. Sci. USA, Vol. 92, pp. 11899–11903, December 1995, and Lim et al. J. Biochem.118, 13–17 (1995). The improved fluorescent variant S65T described by Heim et al. (1995) supra also displays very low fluorescence when incubated under normal culture conditions (37° C.), cf. Kaether and Gerdes FEBS Letters 369 (1995) pp. 267–271. Many experiments involving the study of cell metabolism are dependent on the possibility of incubating the cells at physiologically relevant temperatures, i.e. temperatures at about 37° C.

Thastrup et al. (1997) EP 0 851 874 describes fluorescent proteins that exhibit high fluorescence in cells expressing them when said cells are incubated at a temperature of 30° C. or above. This is obtained with the amino acid in position 1 preceding the chromophore has been mutated. Examples of such mutations are F64L, F64I, F64V F64A and F64G.

Various authors have experimented with combinations of mutations. One such combination is the F64L, S65T GFP (EGFP). EGFP exhibits high fluorescence when expressed at 30° C. or above and has an excitation maximum at 488 nm.

SUMMARY OF THE INVENTION

The present invention provides novel fluorescent proteins, such as F64L-E222G-GFP that result in a cellular fluorescence far exceeding the cellular fluorescence when expressed at 37° C. and when excited at 450 to 500 nm compared to the parent proteins, i.e. GFP, the blue variant Y66H-GFP the S65T-GFP variant, and F64L-GFP. This greatly improves the usefulness of fluorescent proteins in studying cellular functions in living cells.

It is shown that GFP mutated at the 64 position from F to L (F64L) and at the 222 position from E to G (E222G) has remarkable properties. It is first shown that the F64L, E222G-GFP has an entirely different spectrum than F64L, S65T-GFP (Example 2). In contrast, there is no substantial difference between folding characteristics (measured as the time when fluorescence is observed between the two GFPs, Example 3). Likewise, there was no difference between the pH sensitivity of the two GFPs (Example 4). The observed brightness of the E222G versus the S65T mutated F64L-GFPs is dependent on the test conditions (Example 5).

DETAILED DESCRIPTION OF THE INVENTION

One aspect of the present invention relates to a fluorescent protein derived from Green Fluorescent Protein (GFP) or any functional GFP analogue, wherein the amino acid in position 1 preceding the chromophore has been mutated and wherein the Glutamic acid in position 222 has been mutated said mutated GFP has an excitation maximum at a higher wavelength compared to F64L-GFP and the fluorescence is increased when the mutated GFP is expressed in cells incubated at a temperature of 30° C. or above compared to wild-type GFP.

The excitation and emission characteristics of the F64L, E222G-GFP differ significantly from wild-type GFP and EGFP. Existing fluorescent proteins have demonstrated utility for research applications such as quantitative fluorescence microscopy (Patterson, G. H., et al (1997). *Biophysi-* cal J. 73:2782–2790; Piston, D. W.,et al (1999) *Meth. Cell Biol.* 58:31–48). It is now clear, however, that the optimal fluorescent protein characteristics for high-throughput screening (HTS) applications in drug discovery differ somewhat from those for research applications (Kain, S. R. (1999) *Drug Discovery Today* 4:304–312). For example, factors such as optimal and signal/noise are more important for HTS applications in drug discovery than are absolute brightness of probes such as fluorescent proteins. The F64L, E222G-GFP described in this patent application has an excitation maximum of 470 nm and an emission maximum of 505 nm (see FIG. 3:), compared to the respective excitation and emission maxima of 490 nm and 510 nm for EGFP. This results in a Stokes shift of 35 nm for F64L, E222G-GFP, as compared to 20 nm for EGFP. This results in a significant increase in the excitation-emission band separation for F64L,E222G-GFP relative to EGFP with several implications for the use of F64L,E222G-GFP in high-throughput screening. Some of these are listed below:

1. The increased Stokes shift of F64L,E222G-GFP results in increased spectral resolution of its excitation and emission peaks. This enables more complete band separation using a conventional dichroic beam-splitter, and decreased background signal for assays incorporating F64L,E222G-GFP relative to assays based on EGFP.
2. F64L,E222G-GFP fluorescence can be excited by conventional light sources using narrow band filters, or commercially available laser producing lines at 472 nm. In either case, the greater Stokes shift of F64L,E222G-GFP results in lower cross-talk from excitation light to the toe of the emission spectrum.
3. The excitation maximum of F64L,E222G-GFP falls midway between those of the cyan fluorescent protein variant (ECFP, excitation max ~433 nm) and the yellow fluorescent protein variant (EYFP, excitation max ~513 nm). Because of this, it will allow for cleaner band separation when used together with those probes, and it is optimized for assay applications in which several GFP-labeled components will be multiplexed.

Many sources of GFPs exist. Examples are GFP derived from *Aequorea victoria* and GFP derived from *Renilla*. Various GFPs have been isolated from *Renilla* examples are *reniformis* and *mulleri*. As described in the examples and in SEQ ID NOs: 3 and 4, the chromophore in *Aequorea victoria* is in position 65–67 of the predicted primary amino acid sequence of GFP. Thus, in a preferred embodiment the GFP is derived from *Aequorea victoria*.

It is preferred that the mutation at F64 is a mutation to an aliphatic amino acid. Examples are F64L, F64I, F64V, F64A, and F64G, wherein the F64L substitution being most preferred. However other mutations, e.g. deletions, insertions, or post-translational modifications immediately preceding the chromophore are also included in the invention, provided that they result in improved fluorescence properties of the various fluorescent proteins. It should be noted that extensive deletions may result in loss of the fluorescent properties of GFP.

The E222G, E222A, E222V, E222L, E222I, E222F, E222S, E222T, E222N, E222Q substitutions are preferred, the E222G substitution (that is substitution to Glycine) being most preferred.

A preferred sequence of the gene encoding GFP derived from *Aequorea victoria* is disclosed in SEQ ID NO: 3 (enhanced) and in SEQ ID NO: 7 (jelly fish). SEQ ID NO: 1 shows the nucleotide sequence of F64L-GFP with humanised codon. SEQ ID NO: 5 shows the nucleotide sequence of F64L-GFP with jellyfish codon. Besides, the novel fluorescent proteins may also be derived from other fluorescent proteins as mentioned above.

Herein the abbreviations used for the amino acids are those stated in J. Biol. Chem. 243 (1968), 3558.

One aspect of the invention relates to a nucleotide sequence coding for the Fluorescent protein F64L-E222G-GFP. An example of such F64L-E222G-GFP is shown in list 2. In a preferred aspect the nucleotide sequence is in the form of a DNA sequence.

The DNA construct of the invention encoding the novel fluorescent proteins may be prepared synthetically by established standard methods, e.g. the phosphoamidite method described by Beaucage and Caruthers, *Tetrahedron Letters* 22 (1981), 1859–1869, or the method described by Matthes et al., *EMBO Journal* 3 (1984), 801–805. According to the phosphoamidite method, oligonucleotides are synthesized, e.g. in an automatic DNA synthesizer, purified, annealed, ligated and cloned in suitable vectors.

The DNA construct may also be prepared by polymerase chain reaction (PCR) using specific primers, for instance as described in U.S. Pat. No. 4,683,202 or Saiki et al., *Science* 239 (1988), 487–491. A more recent review of PCR methods may be found in *PCR Protocols*, 1990, Academic Press, San Diego, Calif., USA.

The DNA construct of the invention may be inserted into a recombinant vector which may be any vector which may conveniently be subjected to recombinant DNA procedures. The choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the fluorescent protein of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the fluorescent protein of the invention.

The promoter may be any DNA sequence which shows transcriptional activity in the host cell of choice and may be derived from genes encoding proteins either homologous or heterologous to the host cell, including native *Aequorea* GFP genes.

Examples of suitable promoters for directing the transcription of the DNA sequence encoding the fluorescent protein of the invention in mammalian cells are the SV40 promoter (Subramani et al., *Mol. Cell Biol.* 1 (1981), 854–864), the MT-1 (metallothionein gene) promoter (Palmiter et al., *Science* 222 (1983), 809–814) or the adenovirus 2 major late promoter.

An example of a suitable promoter for use in insect cells is the polyhedrin promoter (U.S. Pat. No. 4,745,051; Vasuvedan et al., *FEBS Lett.* 311, (1992) 7–11), the P10 promoter (J. M. Vlak et al., *J. Gen. Virology* 69, 1988, pp. 765–776), the *Autographa californica* polyhedrosis virus basic protein promoter (EP 397 485), the baculovirus immediate early gene 1 promoter (U.S. Pat. Nos. 5,155,037;

5,162,222), or the baculovirus 39K delayed-early gene promoter (U.S. Pat. Nos. 5,155,037; 5,162,222).

Examples of suitable promoters for use in yeast host cells include promoters from yeast glycolytic genes (Hitzeman et al., *J. Biol. Chem.* 255 (1980), 12073–12080; Alber and Kawasaki, *J. Mol. Appl. Gen.* 1 (1982), 419–434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304 (1983), 652–654) promoters.

Examples of suitable promoters for use in filamentous fungus host cells are, for instance, the ADH3 promoter (McKnight et al., *The EMBO J.* 4 (1985), 2093–2099) or the tpiA promoter. Examples of other useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gene, or the *Bacillus pumilus* xylosidase gene, or by the phage Lambda $P_R$ or $P_L$ promoters or the *E. coli* lac, trp or tac promoters.

The DNA sequence encoding the novel fluorescent proteins of the invention may also, if necessary, be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) terminators. The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

The recombinant vector may further comprise a DNA sequence enabling the vector to replicate in the host cell in question. An example of such a sequence (when the host cell is a mammalian cell) is the SV40 origin of replication.

When the host cell is a yeast cell, suitable sequences enabling the vector to replicate are the yeast plasmid 2 μ replication genes REP 1–3 and origin of replication.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125–130), or one which confers resistance to a drug, e.g. ampicillin, kanamycin, tetracyclin, chloramphenicol, neomycin or hygromycin. For filamentous fungi, selectable markers include amdS, pyrG, argB, niaD, sC.

The procedures used to ligate the DNA sequences coding for the fluorescent protein of the invention, the promoter and optionally the terminator and/or secretory signal sequence, respectively, and to insert them into suitable vectors containing the information necessary for replication, are well known to persons skilled in the art (cf., for instance, Sambrook et al., op.cit.).

The host cell into which the DNA construct or the recombinant vector of the invention is introduced may be any cell which is capable of expressing the present DNA construct and includes bacteria, yeast, fungi and higher eukaryotic cells.

Examples of bacterial host cells which, on cultivation, are capable of expressing the DNA construct of the invention are grampositive bacteria, e.g. strains of *Bacillus,* such as *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis,* or strains of *Streptomyces,* such as *S. lividans* or *S. murinus,* or gramnegative bacteria such as *Echerichia coli.* The transformation of the bacteria may be effected by protoplast transformation or by using competent cells in a manner known per se (cf. Sambrook et al., supra).

Examples of suitable mammalian cell lines are the HEK293 and the HeLa cell lines, primary cells, and the COS (e.g. ATCC CRL 1650), BHK (e.g. ATCC CRL 1632, ATCC CCL 10), CHL (e.g. ATCC CCL39) or CHO (e.g. ATCC CCL 61) cell lines. Methods of transfecting mammalian cells and expressing DNA sequences introduced in the cells are described in e.g. Kaufman and Sharp, *J. Mol. Biol.* 159 (1982), 601–621; Southern and Berg, *J. Mol. Appl. Genet.* 1 (1982), 327–341; Loyter et al., *Proc. Natl. Acad. Sci. USA* 79 (1982), 422–426; Wigler et al., *Cell* 14 (1978), 725; Corsaro and Pearson, *Somatic Cell Genetics* 7 (1981), 603, Graham and van der Eb, *Virology* 52 (1973), 456; and Neumann et al., *EMBO J.* 1 (1982), 841–845.

Examples of suitable yeast cells include cells of *Saccharomyces* spp. or *Schizosaccharomyces* spp., in particular strains of *Saccharomyces cerevisiae* or *Saccharomyces kluyveri*. Methods for transforming yeast cells with heterologous DNA and producing heterologous polypeptides therefrom are described, e.g. in U.S. Pat. Nos. 4,599,311, 4,931,373, 4,870,008, 5,037,743, and 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequence encoding the fluorescent protein of the invention may be preceded by a signal sequence and optionally a leader sequence, e.g. as described above. Further examples of suitable yeast cells are strains of *Kluyveromyces,* such as *K. lactis, Hansenula,* e.g. *H. polymorpha,* or *Pichia,* e.g. *P. pastoris* (cf. Gleeson et al., *J. Gen. Microbiol.* 132, 1986, pp. 3459–3465; U.S. Pat. No. 4,882, 279).

Examples of other fungal cells are cells of filamentous fungi, e.g. *Aspergillus* spp., *Neurospora* spp., *Fusarium* spp. or *Trichoderma* spp., in particular strains of *A. oryzae, A. nidulans* or *A. niger.* The use of *Aspergillus* spp. for the expression of proteins is described in, e.g., EP 272 277, EP 230 023, EP 184 438.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptides therein may be performed as described in U.S. Pat. Nos. 4,745,051; 4,879,236; 5,155,037; 5,162, 222; EP 397,485) all of which are incorporated herein by reference. The insect cell line used as the host may suitably be a *Lepidoptera* cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

One aspect of the invention relates to a host transformed with a DNA construct according to any of the preceding aspects. The transformed or transfected host cell described above is then cultured in a suitable nutrient medium under conditions permitting the expression of the present DNA construct after which the cells may be used in the screening method of the invention. Alternatively, the cells may be disrupted after which cell extracts and/or supernatants may be analysed for fluorescence.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection).

In the method of the invention, the fluorescence of cells transformed or transfected with the DNA construct of the invention may suitably be measured in a spectrometer or a fluorescence microscope where the spectral properties of the cells in liquid culture may be determined as scans of light excitation and emission.

One aspect of the invention relates to a fusion compound consisting of a fluorescent protein (F64L-E222G-GFP ), wherein the (F64L-E222G-GFP ) is linked to a polypeptide. Examples of such polypeptide is kinase, preferably the catalytic subunit of protein kinase A, or protein kinase C, or Erk1, or a cytoskeletal element.

The invention further relates to a process for preparing a polypeptide, comprising cultivating a host according to any of the preceding aspects and obtaining therefrom the polypeptide expressed by said nucleotide sequence.

The various aspects of the invention have a plethora of uses. Some of these are described below:

Use of F64L-E222G-GFP in an in vitro assay for measuring protein kinase activity, or dephosphorylation activity, or for measuring protein redistribution.

Use of F64L-E222G-GFP as a protein tag in living and fixed cells. Due to the strong fluorescence the novel proteins are suitable tags for proteins present at low concentrations. Since no substrate is needed and visualisation of the cells does not damage the cells dynamic analysis can be performed.

Use as an organelle tag. More than one organelle can be tagged and visualised simultaneously in living cells, e.g. the endoplasmic reticulum and the cytoskeleton.

Use as a secretion marker. By fusion of F64L-E222G-GFP to a signal peptide or a peptide to be secreted, secretion may be followed on-line in living cells. A precondition for that is that the maturation of a detectable number of novel fluorescent protein molecules occurs faster than the secretion.

Use as genetic reporter or protein tag in transgenic animals. Due to the strong fluorescence of the novel proteins, they are suitable as tags for proteins and gene expression, since the signal to noise ratio is significantly improved over the prior art proteins, such as wild-type GFP.

Use as a cell or organelle integrity marker. By co-expressing two of the novel proteins, the one targeted to an organelle and the other expressed in the cytosol, it is possible to calculate the relative leakage of the cytosolic protein and use that as a measure of cell integrety.

Use as a marker for changes in cell morphology. Expression of the novel proteins in cells allows easy detection of changes in cell morphology, e.g. blebbing, caused by cytotoxic agents or apoptosis. Such morphological changes are difficult to visualize in intact cells without the use of fluorescent probes.

Use as a transfection marker, and as a marker to be used in combination with FACS sorting. Due to the increased brightness of the novel proteins the quality of cell detection and sorting can be significantly improved.

Use as real-time probe working at near physiological concentrations Since F64L-E222G-GFP is significantly brighter than wild type GFP and F64L-GFP when expressed in cells at about 37° C. and excited with light at about 490 nm, the concentration needed for visualization can be lowered. Target sites for enzymes engineered into the novel proteins, e.g. F64L-E222G-GFP, can therefore be present in the cell at low concentrations in living cells. This is important for two reasons: 1) The probe must interfere as little as possible with the intracellular process being studied; 2) the translational and transcriptional apparatus should be stressed minimally.

The novel proteins can be used as reporters to monitor live/dead biomass of organisms, such as fungi. By constitutive expression of F64L-E222G-GFP in fungi the viable biomass will light up.

Transposon vector mutagenesis can be performed using the novel proteins as markers in transcriptional and translational fusions.

Transposons to be used in microorganisms encoding the novel proteins. The transposons may be constructed for translational and transcriptional fusions. To be used for screening for promoters.

Transposon vectors encoding the novel proteins, such as F64L-E222G-GFP, can be used for tagging plasmids and chromosomes.

Use as a reporter for bacterial detection by introducing the novel proteins into the genome of bacteriophages.

By engineering the novel proteins, e.g. F64L-E222G-GFP, into the genome of a phage a diagnostic tool can be designed. F64L-E222G-GFP will be expressed only upon transfection of the genome into a living host. The host specificity is defined by the bacteriophage.

The invention is further illustrated in the following examples with reference to the appended sequence lists.

TABLE 1

List of sequences

| Name | Nucleotide SEQ ID NO: | Protein SEQ ID NO: |
|---|---|---|
| e-F64L-GFP (PS399) | 1 | 2 |
| e-F64L-E222G-GFP (PS699) | 3 | 4 |
| jf-F64L-GFP (PS350) | 5 | 6 |
| jf-F64L-E222G-GFP (PS1186) | 7 | 8 |

LEGEND TO FIGURES

PS codes are explained in Table 2.

FIG. 1 Excitation spectra of PS1189 (excitation maximum at 492 nm), PS1191 (excitation maximum at 468 nm), PS1185 (excitation maximum at 490 nm) and PS1186 (excitation maximum at 473 nm). The emissions were recorded at 560 nm. The samples of PS1189 and PS1191 were 2-fold diluted and the samples of PS1185 and PS1186 were 10-fold diluted.

Figure 2:
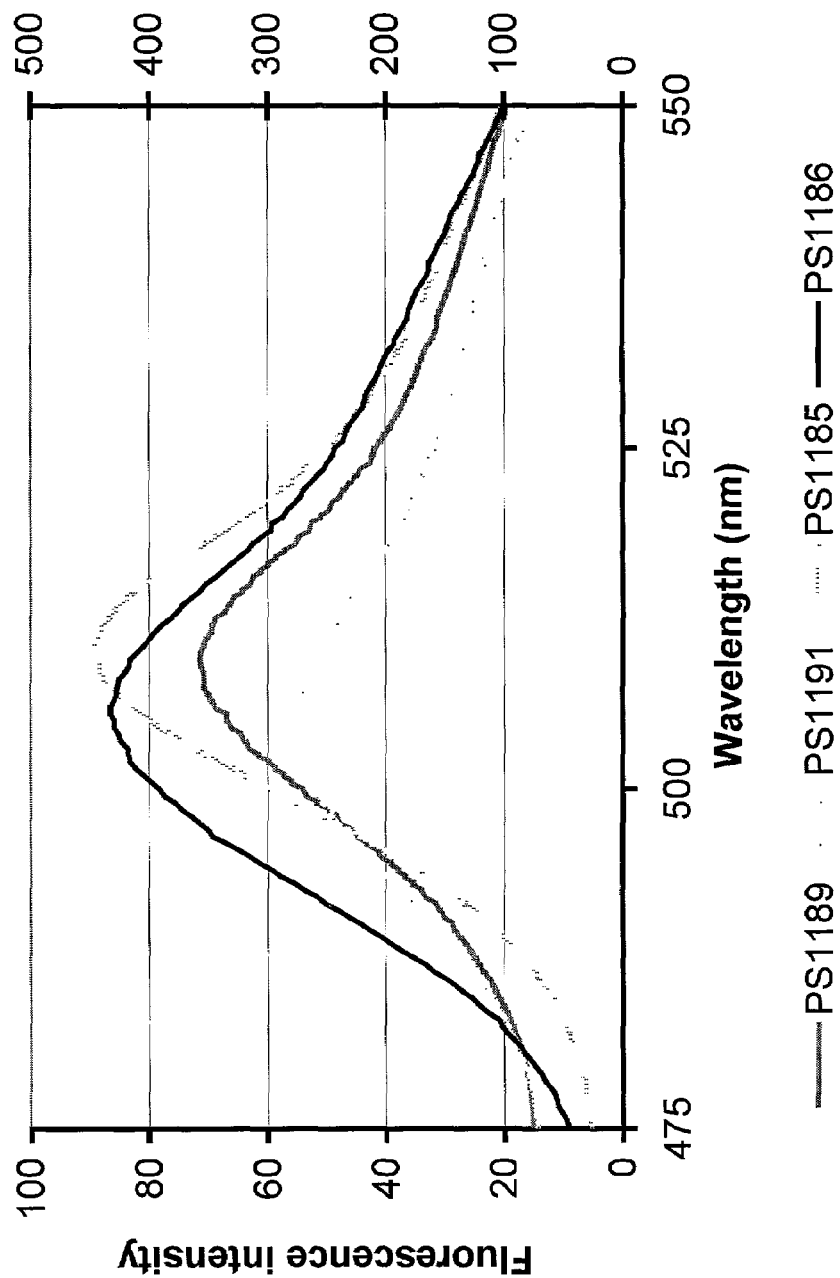

FIG. 2 Emission spectra of PS1189 (emission maximum at 509 nm), PS1191 (emission maximum at 505 nm), PS1185 (emission maximum at 510 nm) and PS1186 (emission maximum at 506 nm). Excitation was at 430 nm. The samples of PS1189, PS1191 and PS1185 were 2-fold diluted and the sample of PS1186 was 10-fold diluted. The curves for PS1189 and PS1191 relate to the primary y-axis whereas the curves for PS1185 and PS1186 relate to the secondary y-axis.

Figure 3:
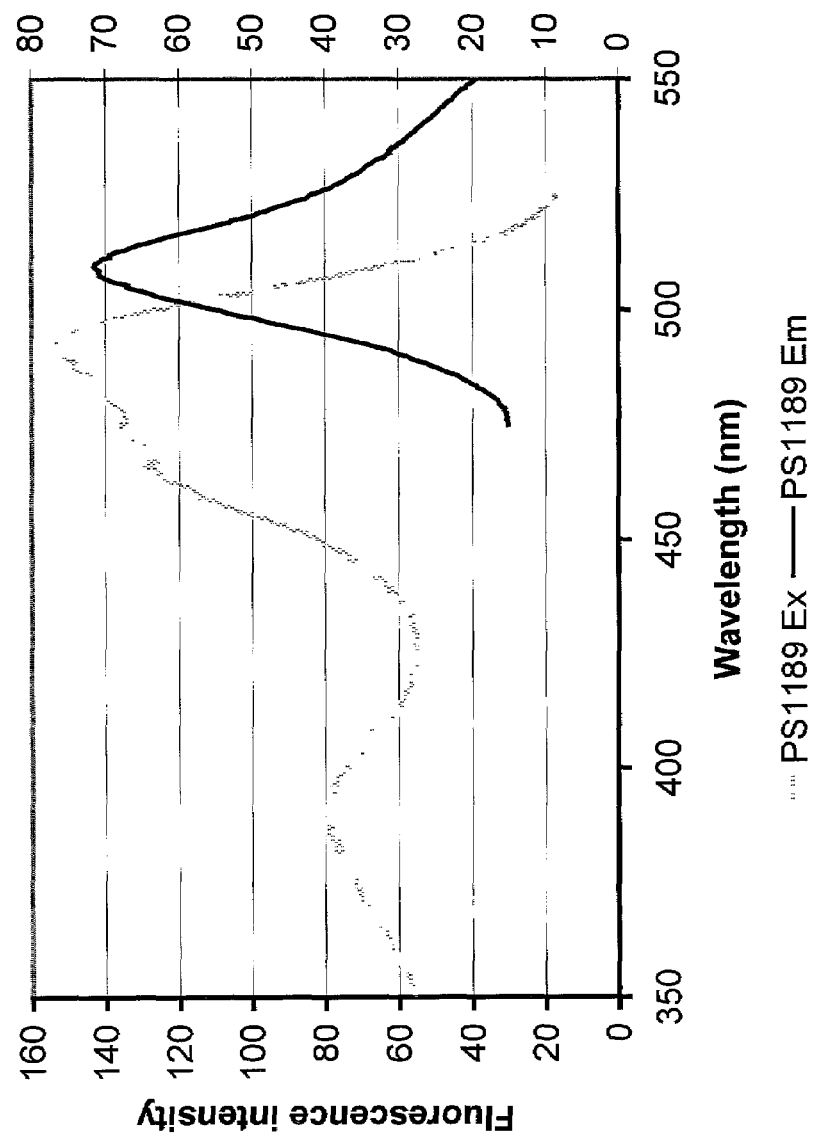
Figure 3:
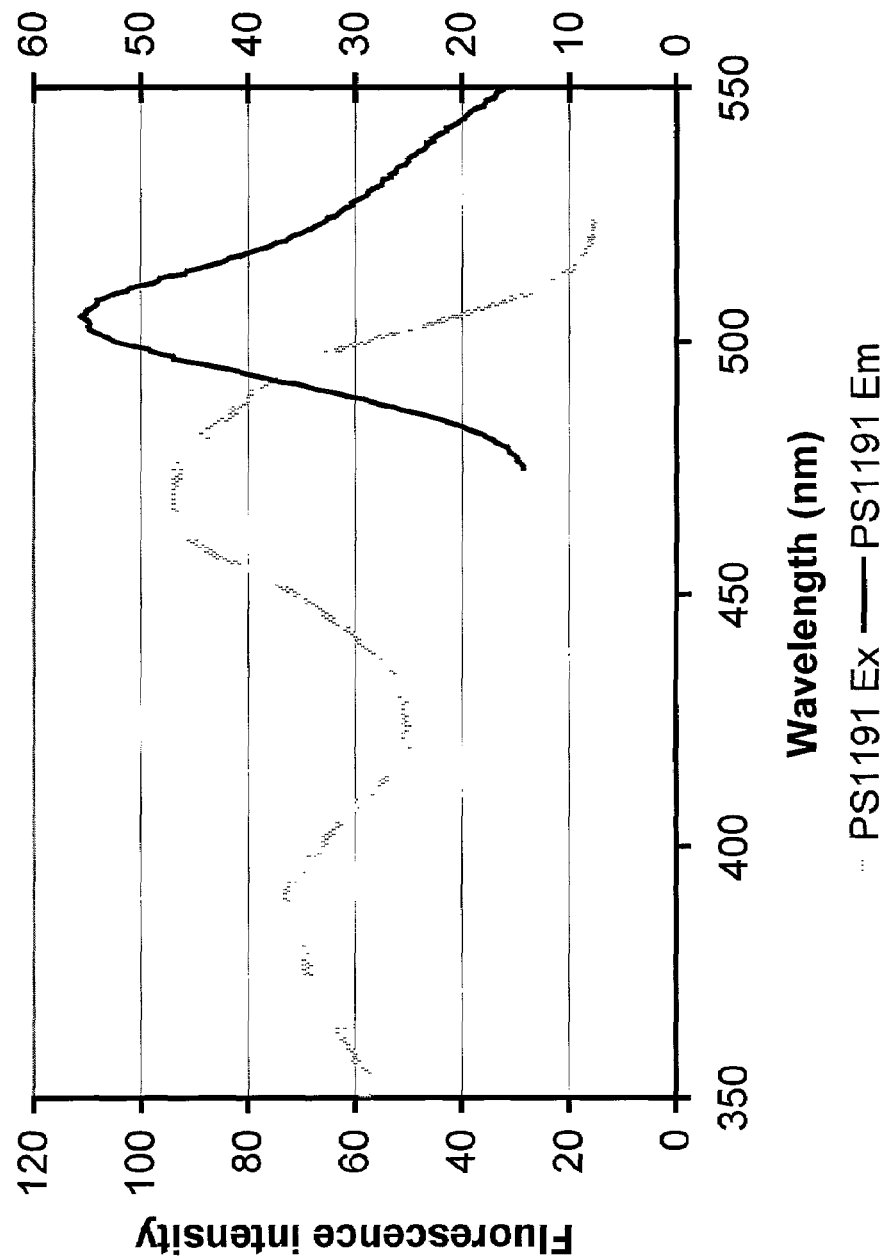
Figure 3:
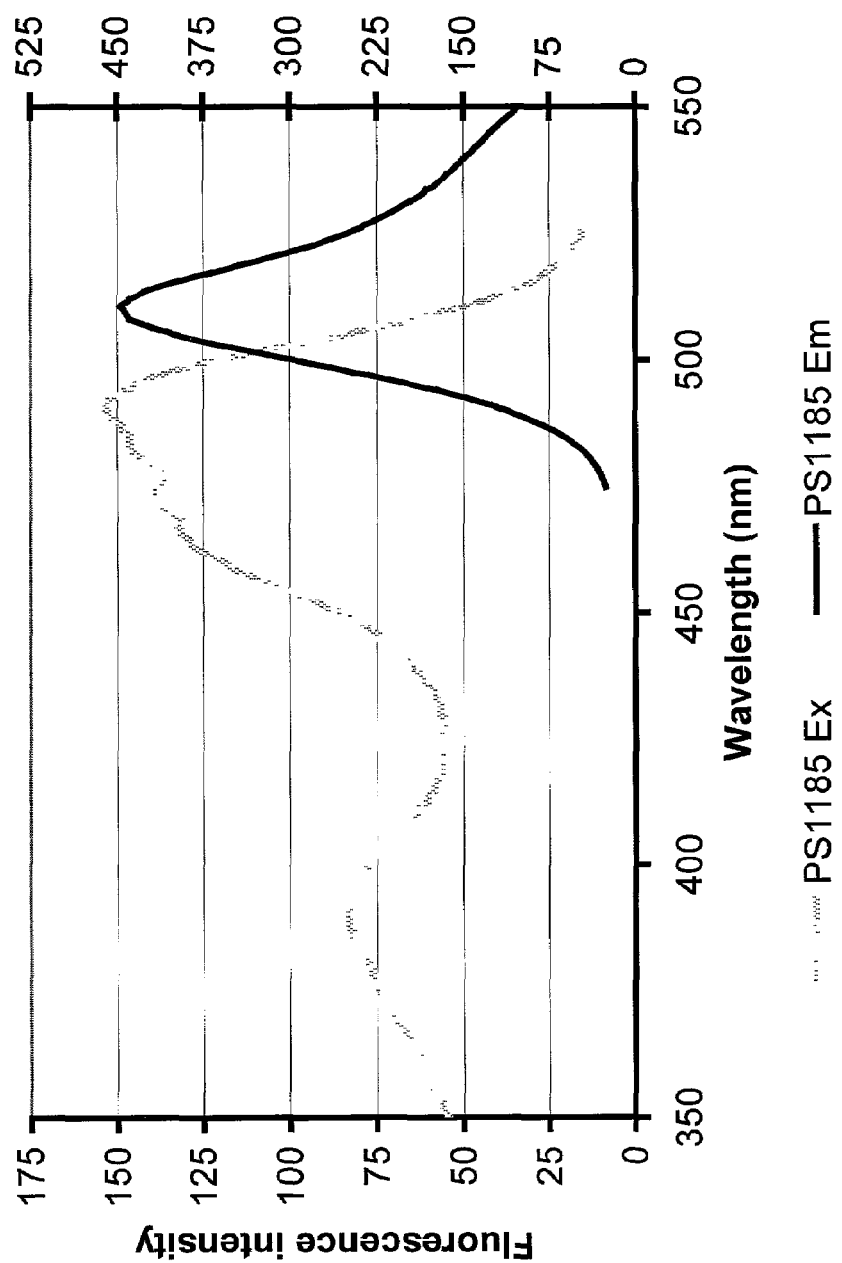
Figure 3:
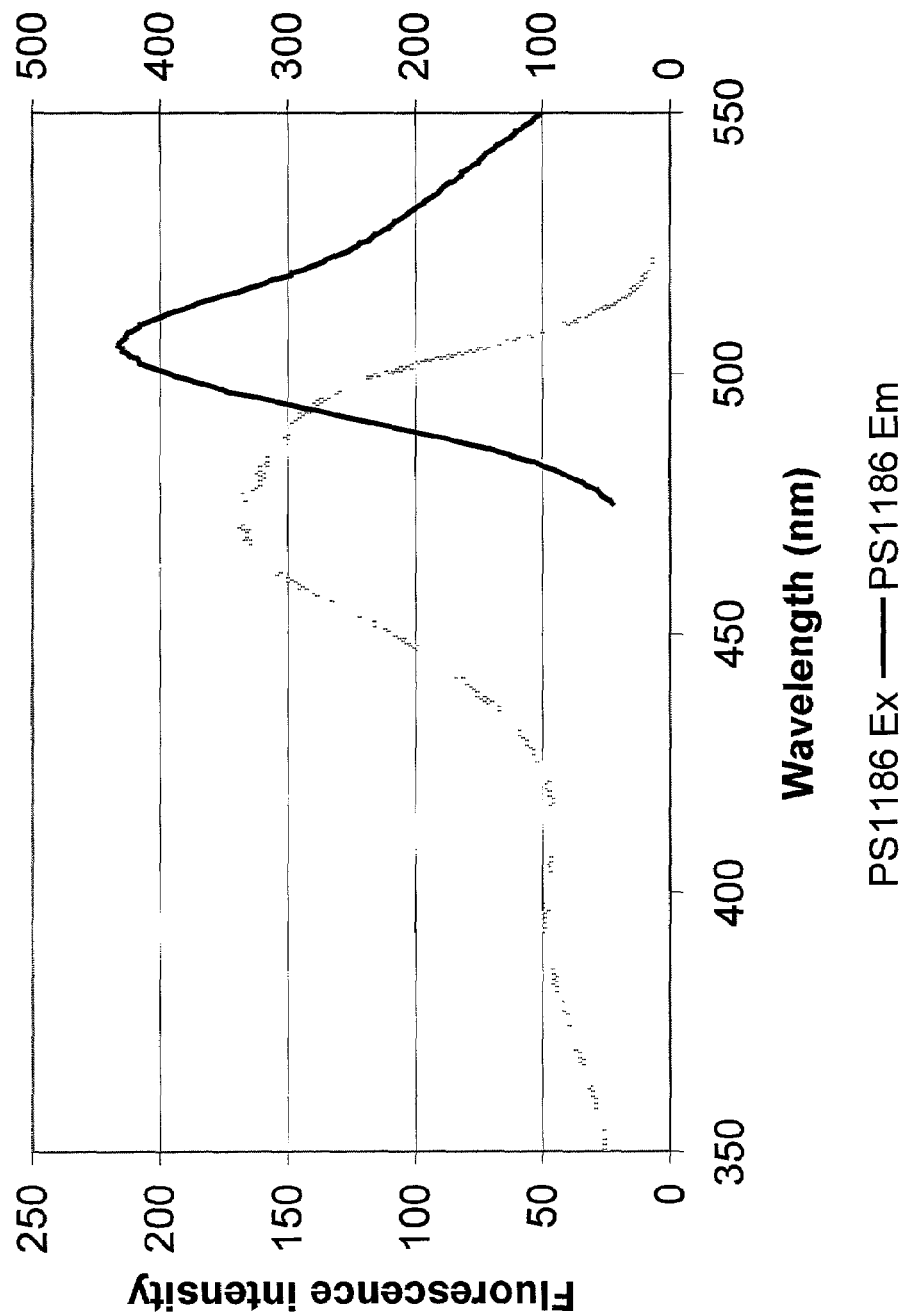

FIG. 3 Overlapping excitation (Ex) and emission (Em) spectra of PS1189 (panel A), PS1191 (panel B), PS1185 (panel C), and PS1186 (panel D). The excitation curve to the left and the excitation curve to the right relate to the primary and secondary y-axis, respectively.

mophore region and introduce a point mutation changing the threonine at position 65 to serine. In addition the primers introduce a unique Spe1 restriction site by silent mutation. The 4.7 kb PCR products were digested with Spe1, religated, and transformed into E.coli. The resulting plasmids are referred to as PS399 (N1 context) and PS401 (C1 context). These plasmids contain the chromophore sequence 64-LSYG-67. Plasmids PS399 and PS401 were subjected to Quick-Change mutagenesis (Stratagene) employing PCR with primers 0225 and 0226 described below. These primers are complementary to sequences near the C-terminus of the GFP and change glutamate at position 222 to glycine, and in addition they introduce an Avr2 restriction site by silent mutation. The resulting plasmids are referred to as PS699 (N1 context) and PS701 (C1 context). They combine an LSYG chromophore with E222G with humanised codon and is referred to as eF64L,E222G (see sequence list 2)

```
9859-top:      5'-TGTACTAGTGACCACCCTGTCTTACGGCGTGCA-3'

9860-bottom:   5'-CTGACTAGTGTGGGCCAGGGCACGGGCAGC-3'

0225-bottom:   5'-CCCGGCGGCGGTCACGAACCCTAGGAGGACCATGTGATCGCG-3'

0226-top:      5'-CGCGATCACATGGTCCTCCTAGGGTTCGTGACCGCCGCCGGG-3'
```

Figure 4:
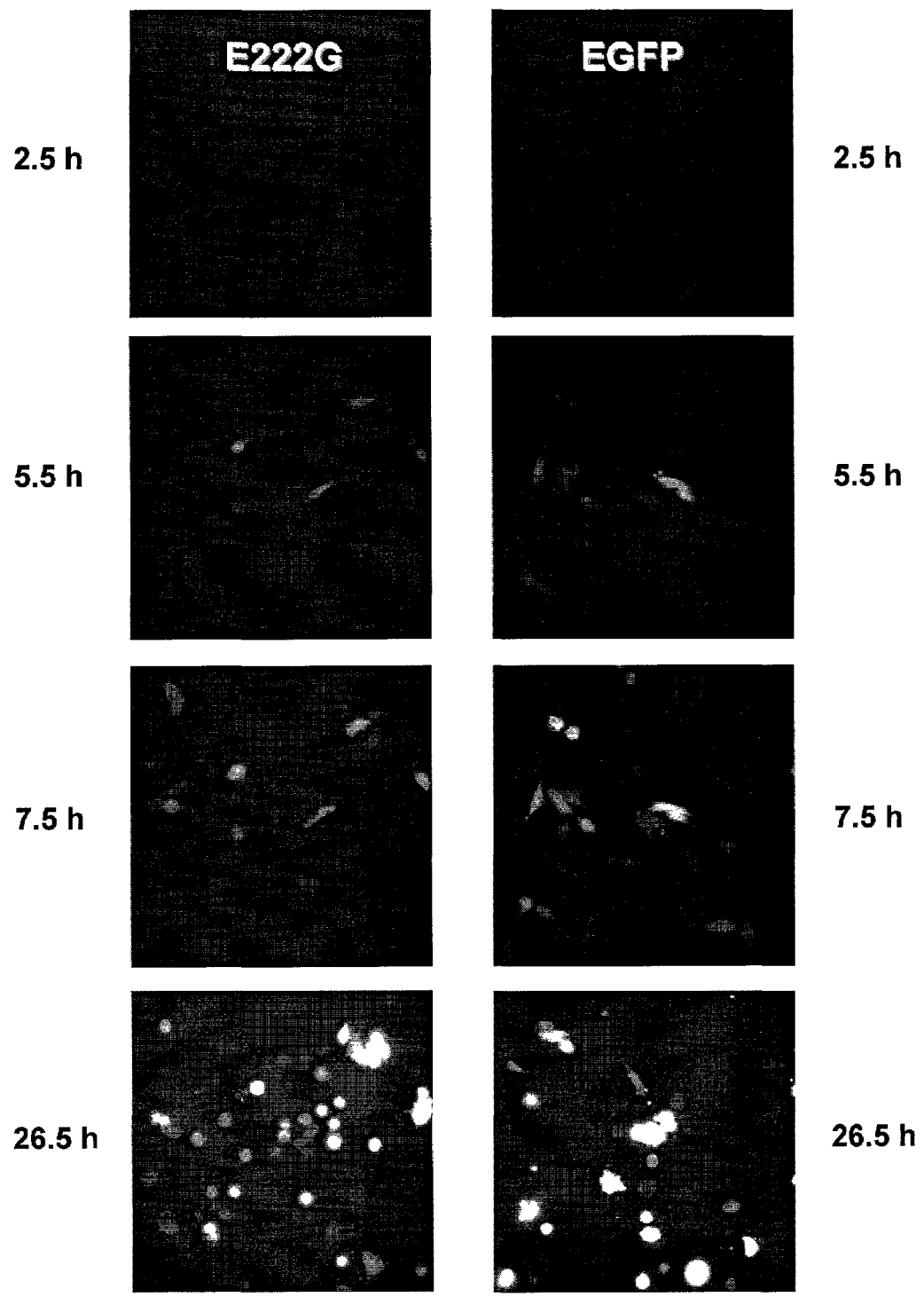

FIG. 4 This figure shows the images collected after Lipofectamine 2000 transfection. eF64L,E222G (PS699) is at the top of the right column referred to as E222G, eF64L,S65T-GFP (PS279) is at the top of the left column referred to as EGFP.

Figure 5:
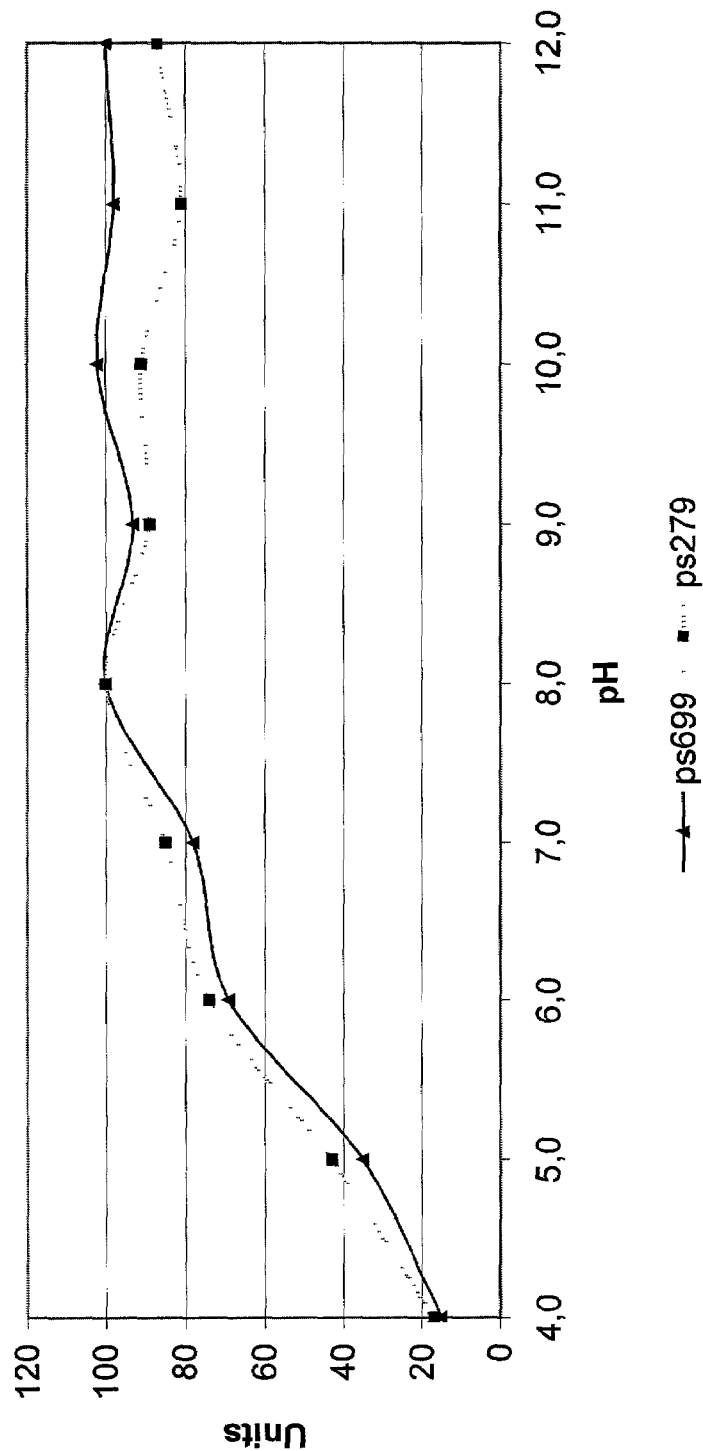

FIG. 5 Comparing the pH sensitivity of EGFP (PS279) and eF64L,E222G-GFP (PS699).

EXAMPLES

Example 1

Construction of GFP Plasmids

Plasmids pEGFP-N1 (GenBank accession number U55762) and pEGFP-C1 (GenBank accession number U55763) both contain a derivative of GFP in which one extra amino acid has been added at position two to provide a better translational start sequence (a Kozak sequence) and so the total number of amino acids is increased by one to 239 instead of the 238 found in wildtype GFP. Therefore the denomination of mutations in GFP in these plasmids strictly should be referred to as e.g. F65L rather than F64L. However, to avoid this source of confusion and because the GFP community has adopted the numbering system of wildtype GFP in its communications, the numbers used here conform to the commonly used naming of mutations in wildtype GFP. The relevant mutations in this respect are F64L, S65T, and E222G.

Plasmids pEGFP-N1 and pEGFP-C1 contain the following mutations in the chromophore: F64L and S65T. The codon usage of the GFP DNA sequence has been optimized for expression in mammalian cells. N1 and C1 refer to the position of multiple cloning sites relative to the GFP sequence.

To construct a plasmid combining F64L and E222G, pEGFP-N1 and pEGFP-C1 were first subjected to PCR with primers 9859 and 9860 described below. The primers are complementary to the DNA sequence around the chro- A plasmid encoding a GFP directly derived from jellyfish with F64L (disclosed in FIG. 4 of WO97/11094,) was subjected to PCR with primers 9840 & 9841 described below. The PCR product was digested with restriction enzymes Age1 and Acc65 and ligated into pEGFP-N1 digested with Age1 and BsrG1. This replaces EGFP with F64L-GFP and introduces an amino acid change L236G near the c-terminus as a consequence of joining Acc65 and BsrG1 sites. This plasmid is referred to as PS350.

A plasmid encoding a GFP directly derived from jellyfish with F64L, S65T (disclosed in FIG. 5 of WO97/11094,) was subjected to PCR with primers 9840 & 9841 described below. The PCR product was digested with restriction enzymes Age1 and Acc65 and ligated into pEGFP-N1 digested with Age1 and BsrG1. This replaces EGFP with F64L, S65T-GFP and introduces an amino acid change L236G near the c-terminus as a consequence of joining Acc65 and BsrG1 sites. This plasmid is referred to as PS351.

Plasmid PS350 was subjected to QuickChange PCR (Stratagene) with primers 0317 & 0318 described below. This introduces E222G by mutation and an Avr2 restriction site by silent mutation. This plasmid is referred to as PS832.

Plasmid PS832 was subjected to QuickChange PCR (Stratagene) with primers 0325 & 0326 described below. This introduces L64F by mutation and a Psp1406 restriction site by silent mutation. This plasmid is referred to as PS845.

A plasmid encoding a GFP directly derived from jellyfish (disclosed in FIG. 2a of WO97/11094) was subjected to PCR with primers 9840 & 9841 described below. The PCR product was digested with restriction enzymes Age1 and Acc65 and ligated into pEGFP-N1 digested with Age1 and BsrG1. This replaces EGFP with wildtype GFP and introduces an amino acid change L236G near the c-terminus as a consequence of joining Acc65 and BsrG1 sites. This plasmid is referred to as PS854.

Plasmid PS399 was subjected to QuickChange PCR (Stratagene) with primers 0327 & 0328 described below. This introduces L64F by mutation and a Psp1406 restriction site by silent mutation. This plasmid is referred to as PS844.

Plasmid PS699 was subjected to QuickChange PCR (Stratagene) with primers 0327 & 0328 described below. This introduces L64F by mutation and a Psp1406 restriction site by silent mutation. This plasmid is referred to as PS846.

The plasmids described above were transformed into E.coli strain DH5alpha (Life Technologies). Single colonies were picked and grown overnight at 37C in LB medium containing 1 mM IPTG. 0.5 ml cells were pelleted and stored at −20C until they were analyzed.

```
9840-top:      5'-GTACCGGTCACCATGAGTAAAGGAGAAGAAC-3'

9841-bottom:   5'-TTATTGGTACCCTTCATCCATGCCATGTG-3'

0317-top:      5'-GAGATCACATGATCCTCCTAGGGTTTGTAACAGCTGCTGGG-3'

0318-bottom:   5'-CCCAGCAGCTGTTACAAACCCTAGGAGGATCATGTGATCTC-3, 0325-top:      5'-CCAACGCTTGTCACAACGTTTTCTTATGGTGTTC-3'

0326-bottom:   5'-GAACACCATAAGAAAACGTTGTGACAAGCGTTGG-3'

0327-top:      5'-CCCACACTAGTGACAACGTTTTCTTACGGCGTGC-3'

0328-bottom:   5'-GCACGCCGTAAGAAAACGTTGTCACTAGTGTGGG-3'
```

Plasmids encoding GFPs in jellyfish codon context (PS350, PS351, PS832, PS845, PS854) were subjected to PCR with primers 1259 and 1260 described below. The ca 0.8 kb PCR products were cut with restriction enzymes BspH1 and BamH1, and ligated into E.coli expression vector pTrcHis (from Invitrogen) cut with Nco1 and BamH1. This places the GFPs under control of the ITPG-inducible promoter in the vector. The bottom primer 1260 also changes the glycine at position 236 back to leucine. The resulting plasmids are referred to as PS1184 (jf-F64L-GFP), PS1185 (jf-F64L,S65T-GFP), PS1186 (jf-F64L,E222G-GFP), PS1187 (jf-E222G-GFP) and PS (jf-GFP).

Plasmids encoding GFPs in humanised enhanced codon context (PS279=pEGFP-N1 (Clontech), PS399, PS699, PS844, PS846) were subjected to PCR with primers 1261 and 1262 described below. The ca 0.8 kb PCR products were cut with restriction enzymes Nco1 and BamH1, and ligated into E.coli expression vector pTrcHis (from Invitrogen) cut with Nco1 and BamH1. This places the GFPs under control of the ITPG-inducible promoter in the vector. The resulting plasmids are referred to as PS1189 (e-F64L,S65T-GFP=EGFP), PS1190 (e-F64L-GFP), PS1191 (e-F64L,E222G-GFP), PS1192 (e-GFP) and PS1193 (e-E222G-GFP).

```
1259-top:      5'-GTTGTTTCATGAGTAAAGGAGAAGAACTTTTC-3'

1260-bottom:   5'-GTTGGATCCTTATTTGTATAGTTCATCCATG-3'

1261-top.      5'-GTTGTTCCATGGTGAGCAAGGGCGAGGAGCTG-3'

1262-bottom:   5'-GTTGGATCCTTACTTGTACAGCTCGTCCATG-3'
```

TABLE 2

Summary table of plasmids encoding GFPs with indicated amino acids at positions 64, 65 and 222.

| mammalian cell expression plasmid | Backbone-codon usage | aa pos 64 | aa pos 65 | aa pos 222 | E. coli expression plasmid |
|---|---|---|---|---|---|
| PS846 | e-E222G-GFP | enhanced | F | S | G | PS1193 |
| PS844 | e-GFP | enhanced | F | S | E | PS1192 |
| PS699 | e-F64L,E222G-GFP | enhanced | L | S | G | PS1191 |
| PS399 | e-F64L-GFP | enhanced | L | S | E | PS1190 |
| PS279 | EGFP | enhanced | L | T | E | PS1189 |
| PS854 | jf-GFP | jellyfish | F | S | E | P51188 |
| PS845 | jf-E222G-GFP | jellyfish | F | S | G | PS1187 |
| PS832 | jf-F64L,E222G-GFP | jellyfish | L | S | G | PS1186 |
| PS351 | jf-F64L,S65T-GFP | jellyfish | L | T | E | PS1185 |
| PS350 | jf-F64L-GFP | jellyfish | L | S | E | PS1184 |

Example 2

Determination of Spectral Properties of Proteins EGFP and eF64L,E222G

Plasmids expressing EGFP from plasmid pEGFP-N1 (also referred to as PS279), and eF64L,E222G from plasmid PS699 were transfected into E.Coli TOP10 cells (Invitrogen) using lipofectamine 2000 (from Life Technologies) according to manufacturers recommendations. After 5 days cells were collected and resuspended in extraction buffer 50 mM TRIS(pH 8.0) with 1 mM DTT. Cells were lysed by 3 cycles of freeze-thaw. Cell debris was centrifuged out at 10000 g in acooled centrifuge. NaCl was added to 100 mM.

The cell pellets were resuspended in 1000 μl of $H_2O$ each (2-fold dilution relative to volumes of pelleted cultures) and transferred to 1.0×0.5 cm plastic cuvettes and the following excitation and emission spectra were recorded on a Perkin Elmer LS50B luminescence spectrometer:

Excitation spectrum:

Excitation at 350–525 nm (5 nm slit width)  Emission 560 nm (10 nm slit width)
Data presented in FIG. 1.

Emission spectrum:

Excitation at 430 nm (10 nm slit width)  Emission 450–550 nm (5 nm slit width)
Data presented in FIG. 2.

Using the same settings, excitation and emission spectra of 10-fold (200 μl of 2-fold diluted cells mixed with 800 μl of water) diluted cells were recorded for the strongly fluorescent samples expressed from cDNAs with jellyfish backbone (PS1185 and PS1186).

In contrast to the expression levels, the fluorescence properties of the probes were independent of the codon usage. The spectra recorded for the probes with Thr65:E222 (PS1185 and PS1189) were very similar (excitation and emission maxima at 490–492 nm and 509–510 nm, respectively) and with Stokes shifts of 17–20 nm. Likewise, the spectra recorded for the probes with Ser65:G222 (PS1186 and PS1191) were very similar (excitation and emission maxima at 468–473 nm and 505–506 nm, respectively) and with Stokes shifts of 33–37 nm.

Example 3

Determination of Time to Fluorescence of EGFP and eF64L,E222G in CHO Cells

Three, 2 well chambers with CHOhIR cells were transfected with plasmid PS279 expressing EGFP and plasmid PS699 expression eF64L,E222G using the Lipofectamine transfection method.

Fluorescence from the cells was checked at regular intervals after transfection.

Lipofectamine 2000 transfection method was used to transfect EGFP and eF64L,E222G in one, 8-well chamber with CHOhIR cells. Fluorescence from the cells was checked at regular intervals after transfection as described above. Images were taken from the same cell fields at each interval. Three different fields were observed for each plasmid. The microscope and camera settings were the same for each image. Optimal exposure time was taken from a chamber of cells with full EGFP expression (transfected 24 hours previously) to ensure the exposure does not saturate. The first images were taken from 45 minutes to 1 hour post transfection, thereafter with a 30-minute interval for the first 7.5 hours post transfection and an image was collected 26.5 hours post transfection. Five different fields were observed for each plasmid. Fluorescence was detected no later then 4 hours post transfection. Fluorescence in eF64L,E222G was detected in one field 2.5 hours post transfection. In the remaining fields, fluorescence was detected no later than 4 hours post transfection (FIG. 4).

Example 4

Comparing pH Sensitivity Over Range pH 4.0 to pH 12.0 between EGFP and eF64L,E222G Samples of semi-purified EGFP from PS279 and eF64L,E222G from PS699 proteins produced in COS7 cell expression are tested for pH sensitivity over a range from pH 4.0 to pH 12.5, with 0.5 point intervals. Excitation and emission scans were taken of each protein at the pH values of 4.0, 8.0, and 12.5. The results of the scans found EGFP's excitation max to be 490 nm and emission max to be 510 nm and eF64L,E222G 's excitation max to be 475 nm and emission max to be 504 nm. Different pH values did not affect the excitation or emission max. Single reads were made with excitation at 470 nm, emission at 510 nm and with 10 nm slits. The results show no clear differences between EGFP and eF64L,E222G regarding pH sensitivity, except what could be due to random fluctuation (FIG. 5). This experiment has been repeated with essentially same result.

Example 5

Comparison of Relative Brightness of GFPs 10 plasmids were constructed which combine some of the following features:
F or L at position 64.
S or T at position 65.
E or G at position 222.
"jellyfish" or "humanised enhanced" GFP backbone.

The plasmids were transfected into CHO cells. One, two and four days later the cells were inspected visually in a fluorescence microscope by two people. The excitation was 475/40=blue light and the emission 510–560=green light. Cells were scored on a "green" scale ranging from essentially black to extremely bright (Table 3). Results did not change much with time.

TABLE 3

| Plasmid | "greenness" | GFP (* UVmax) | codon context | aa 64 | aa 65 | aa 222 |
|---|---|---|---|---|---|---|
| PS854 | black | jf-GFP * | jellyfish | F | S | E |
| PS845 | almost black | jf-GFP-E222G | jellyfish | F | S | G |
| PS846 | almost black | e-GFP-E222G | humanised | F | S | G |
| PS844 | almost black | e-GFP * | humanised | F | S | E |
| PS350 | light green | jf-GFP-F64L * | jellyfish | L | S | E |
| PS351 | green | jf-GFP-S65T | jellyfish | L | T | E |
| PS832 | green | jf-GFP-F64L,E222G | jellyfish | L | S | G |
| PS399 | bright green | e-GFP-F64L * | humanised | L | S | E |
| PS699 | very bright green | e-GFP-F64L,E222G | humanised | L | S | G |
| PS279 | very bright green | EGFP | humanised | L | T | E |

The plasmids were also transfected into HeLa cells. After 24 hours transfection the cells were run on a FACS Calibur flow cytometer for characterisation of whole cell fluorescence, with excitation at 488 nm and emission viewed with fluorescence filter set 530/30 nm (range 515–545 nm). 10000 events were collected for each transfection and 2 replicates carried out for each construct. Average fluorescent intensities from the FACS analysis were obtained as geometric means (mean fluorescence on log scale) and results are shown in Table 4.

TABLE 4

| Plasmid | FACS | GFP (* UVmax) | codon context | aa 64 | aa 65 | aa 222 |
|---|---|---|---|---|---|---|
| PS845 | 5.4 | jf-GFP-E222G | jellyfish | F | S | G |
| PS854 | 5.5 | jf-wtGFP * | jellyfish | F | S | E |
| PS350 | 9.3 | jf-BioGreen * | jellyfish | L | S | E |

TABLE 4-continued

| Plasmid | FACS | GFP (* UVmax) | codon context | aa 64 | aa 65 | aa 222 |
|---|---|---|---|---|---|---|
| PS846 | 9.4 | e-wtGFP-E222G | humanised | F | S | G |
| PS832 | 16.5 | jf-BioE222G | jellyfish | L | S | G |
| PS351 | 22.2 | jf-BioST | jellyfish | L | T | E |
| PS844 | 24.5 | e-wtGFP * | humanised | F | S | E |
| PS399 | 73.3 | e-BioGreen * | humanised | L | S | E |
| PS699 | 209.2 | e-BioE222G | humanised | L | S | G |
| PS279 | 421 | EGFP | humanised | L | T | E |

It is clear from the table above that, when expressed in the mammalian HeLa cell, the GFPs with humanised codon are far brighter than the GFPs with jellyfish codon. EGFP and e-BioE222G being the brightest. It is no surprise that EGFP is about twice as bright as E-BioE222G under these conditions. The excitation at the FACS is at 488 nm, close the excitation maximum of EGFP at 490 nm. As illustrated in Table 5 below 97% of the emission from EGFP will be picked up, whereas only 86% from the e-BioE222G. Furthermore, the difference between the intensity of EGFP and e-bioE222G when excited at the e-bioE222G excitation maximum of 470 is not as pronounced.

TABLE 5

|  | PS1189 eLTE | PS1191 eLSG | PS1185 jfLTE | PS1186 jfLSG |
|---|---|---|---|---|
| Emission intensity with excitation at 470 nm | 131.4 | 94.1 | 155.0 | 167.2 |
| Emission intensity with excitation at 488 nm | 148.1 | 80.4 | 178.2 | 151.2 |
| Excitation max | 492 nm | 468 nm | 490 nm | 473 nm |
| Emission intensity at excitation max | 152.9 | 93.8 | 183.3 | 169.1 |
| Ratio: Em. intensity(488)/Em. intensity(max) | 0.97 | 0.86 | 0.97 | 0.89 |
| Emission max | 509 nm | 505 nm | 510 nm | 506 nm |
| Emission intensity at emission max | 71.2 | 55.6 | 444 | 432 |

In mammalian cells enhanced GFPs were brighter than jellyfish GFPs. In E.Coli. jellyfish GFPs were brighter than enhanced GFPs. Thus, when it is worthwhile to choose the GFP backbone with care according to the subsequent host.

What is claimed is:

1. A fluorescent protein, as shown in SEQ ID NO: 4, wherein the amino acid in position 1 preceding the chromophore has been substituted by an aliphatic amino acid, and wherein the Glutamic acid in position 223 has been substituted by an amino acid selected from the group consisting of G, A, V. L and I.

2. A fluorescent protein according to claim 1, wherein the chromophore is in position 66–68 of the predicted primary amino acid sequence of GEP as shown in SEQ ID NO: 4.

3. A fluorescent protein according to claim 1 or 2, said protein being derived from *Aequorea victoria* or *Renilla*.

4. A fluorescent protein according to claim 1, wherein the amino acid F in position 65 of the GFP has been substituted by an aliphatic amino acid.

5. A fluorescent protein according claim 1, wherein the amino acid F in position 65 of the GFP has been substituted by an amino acid selected from the group consisting of L, I, V. A and G.

6. A fluorescent protein according to claim 1, wherein the amino acid F in position 65 of the GFP has been substituted by L.

7. A fluorescent protein according to claim 1, wherein the amino acid E in position 223 of the GFP has been substituted by G.

8. A fluorescent protein according to claim 1 having the amino acid sequence disclosed in SEQ ID NO: 4.

9. A fusion compound comprising a fluorescent protein (GFP) according to claim 1, wherein the GFP is linked to a polypeptide.

10. A fusion compound according to claim 9, wherein the polypeptide is a kinase or a cytoskeletal element.

11. A fusion compound according to claim 10, wherein the polypeptide is the catalytic subunit of protein kinase A, protein kinase C, or Erkl.

12. A fluorescent protein according to claim 1, wherein the amino acid E in position 223 of the GFP has been substituted by an amino acid selected from the group consisting of A, V, L and I.

13. A fluorescent protein, comprising a Green Fluorescent Protein (GFP) comprising an amino acid sequence wherein the amino acid at the position corresponding to position 65 of SEQ ID NO:4 is substituted with an aliphatic amino acid, and wherein the amino acid at the position corresponding to the position 223 of SEQ ID NO:4 has been substituted by an amino acid selected from the group consisting of G, A, V, L and I.

* * * * *

UNITED STATES PATENT AND TRADEMARK OFFICE
CERTIFICATE OF CORRECTION

PATENT NO. : 7,001,986 B2
APPLICATION NO. : 09/887784
DATED : February 21, 2006
INVENTOR(S) : Sara P. Bjorn et al.

It is certified that error appears in the above-identified patent and that said Letters Patent is hereby corrected as shown below:

On the title page, Item (60), line 3, please correct the following:

"May 10, 2001" to --May 9, 2001-- col. 33, line 28, Claim 2, change "GEP" to --GFP--. **

Signed and Sealed this

Fifth Day of September, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,001,986 B2 |
| APPLICATION NO. | : 09/887784 |
| DATED | : February 21, 2006 |
| INVENTOR(S) | : Sara P. Bjorn et al. |

It is certified that error appears in the above-identified patent and that said Letters Patent is hereby corrected as shown below:

On the front page of the patent, Item (60), please correct the following:

"May 10, 2001" to --May 9, 2001--

Signed and Sealed this

Third Day of October, 2006

JON W. DUDAS
*Director of the United States Patent and Trademark Office*